United States Patent [19]

Audeh

[11] 4,303,791
[45] Dec. 1, 1981

[54] 1-METHYL OR PROPYL ORGANIC NITROGEN COMPOUNDS AND METHOD OF PREPARATION

[75] Inventor: Costandi A. Audeh, Princeton, N.J.

[73] Assignee: Mobil Oil Corporation, New York, N.Y.

[21] Appl. No.: 73,766

[22] Filed: Sep. 10, 1979

[51] Int. Cl.³ .............................................. C07D 487/08
[52] U.S. Cl. .................................... 544/351; 423/328; 423/329
[58] Field of Search .......................................... 544/351

[56] References Cited

U.S. PATENT DOCUMENTS

| | | | |
|---|---|---|---|
| 3,038,903 | 6/1962 | Farkas et al. | 544/351 |
| 3,167,555 | 1/1965 | Farkas et al. | 544/351 |
| 3,247,195 | 4/1966 | Kerr | 423/328 X |
| 3,459,676 | 8/1969 | Kerr | 423/329 X |
| 3,692,470 | 9/1972 | Ciric | 423/328 |
| 3,702,886 | 11/1972 | Argauer et al. | 423/328 |
| 4,061,717 | 12/1977 | Kerr et al. | 423/329 |
| 4,079,014 | 3/1978 | Burness et al. | 544/351 |
| 4,100,262 | 7/1978 | Pelrine | 423/328 |
| 4,175,114 | 11/1979 | Plank et al. | 423/328 |

OTHER PUBLICATIONS

Farkas et al., "Journal of Chem. Eng.-Data", vol. 13 (1963), pp. 278–284.

*Primary Examiner*—Donald G. Daus
*Assistant Examiner*—James H. Turnipseed
*Attorney, Agent, or Firm*—Charles A. Huggett; Michael G. Gilman; Charles J. Speciale

[57] ABSTRACT

New compounds 1-alkyl, 4-aza, 1-azonia-bicyclo (2,2,2)octane, 4-oxide, halides useful as templates for the formation of crystalline zeolites and process for preparing said new compounds from diazobicyclooctane.

1 Claim, No Drawings

1-METHYL OR PROPYL ORGANIC NITROGEN COMPOUNDS AND METHOD OF PREPARATION

BACKGROUND OF THE INVENTION

1. Field of the Invention

This invention relates to organic nitrogen compounds useful in preparing crystalline zeolite materials and more particularly to a new class of compounds 1-alkyl, 4-aza, 1-azonia-bicyclo(2,2,2) octane, 4-oxide, halides and a method for preparing same.

2. Description of the Prior Art

Zeolitic materials, both natural and synthetic, have been demonstrated in the past to have catalytic properties for various types of hydrocarbon conversions. Certain zeolitic materials are ordered, porous crystalline aluminosilicates having a definite crystalline structure within which there are a large number of channels. These cavities and channels are precisely uniform in size. Since the dimensions of these pores are such as to accept for adsorption molecules of certain dimensions while rejecting those of larger dimensions, these materials have come to be known as "molecular sieves" and are utilized in a variety of ways to take advantage of these properties.

Such molecular sieves, both natural and synthetic, include a wide variety of positive ion-containing crystalline aluminosilicates. These aluminosilicates can be described as a rigid three-dimensional framework of $SiO_4$ and $AlO_4$ in which the tetrahedra are cross-linked by the sharing of oxygen atoms whereby the ratio of the total aluminum and silicon atoms to oxygen is 1:2. The electrovalence of the tetrahedra containing aluminum is balanced by the inclusion in the crystal of a cation, for example, an alkali metal or an alkaline earth metal cation. This can be expressed wherein the ratio of aluminum to the number of various cations, such as $Ca/2$, $Sr/2$, Na, K or Li is equal to unity. One type of cation may often be exchanged either entirely or partially by another type of cation utilizing ion exchange techniques in a conventional manner. By means of such cation exchange, it has been possible to vary the properties of a given aluminosilicate by suitable selection of the cation. The spaces between the tetrahedra are usually occupied by molecules of water prior to dehydration.

Prior art techniques have resulted in the formation of a great variety of synthetic aluminosilicates. These aluminosilicates have come to be designated by letter or other convenient symbols, as illustrated by zeolite A (U.S. Pat. No. 2,882,243), zeolite X (U.S. Pat. No. 2,882,244), zeolite Y (U.S. Pat. No. 3,130,007), zeolite ZK-5 (U.S. Pat. No. 3,247,195), zeolite ZK-4 (U.S. Pat. No. 3,314,752) zedite ZSM-5 (U.S. Pat. No. 3,702,886), zeolite ZSM-11 (U.S. Pat. No. 3,709,979), zeolite ZSM-12 (U.S. Pat. No. 3,832,449), ZSM-35 (U.S. Pat. No. 4,016,245), zeolite ZSM-21 and 38 (U.S. Pat. No. 4,046,859), and zeolite ZSM-23 (U.S. Pat. No. 4,076,842), merely to name a few.

SUMMARY OF THE INVENTION

The novel class of compounds described hereinbelow, useful in zeolite synthesis have heretofore not been known. The present invention relates to a novel class of compounds, 1-alkyl, 4-aza, 1-azonia-bicyclo(2,2,2) octane, 4-oxide, halides useful as templates in zeolite synthesis. In this connection see co-pending U.S. Application Ser. No. 073,765, filed on Sept. 10, 1979. These compounds are also potentially useful as fuel anti-static agents. This new class of organic compounds combines ionic salt character and covalent character of two nitrogen atoms in the same molecule. One nitrogen carries a formal positive charge being quaternary in nature, while the other, covalently bonded to oxygen, is not. They are soluble in water and form a stable solution in a high pH environment. The structure is postulated as follows:

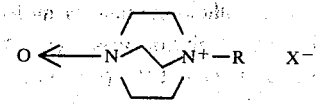

wherein R is alkyl and x is halide.

Preparation of the new class of compounds is derived from diazabicyclooctane commercially available as DABCO commercially available.

DESCRIPTION OF PREFERRED EMBODIMENTS

Preparation of the subject compounds is accomplished by a procedure involving the steps of:

(1) dissolving 1,4-diazabicyclo(2,2,2) octane in toluene or benzene and then adding aqueous hydrogen peroxide to form two layers, aqueous and organic (2) separating the aqueous layer and mixing same with water and evaporating to dryness under reduced pressure yielding a solid compound (3) treating the solid of step (2) with toluene or benzene to remove any unreacted starting material, returning the resultant liquid treat to the organic layer of step (1) drying the resultant mixture over a drying agent, e.g. silica, silica-alumina, or a zeolite and repeating step (1) on the dried toluene solution.

(4) subjecting the solid compound of step (2) to heating under reduced pressure yielding a resultant solid compound (5) dissolving the compound of step (4) in anhydrous ethanol, methanol or acetone (6) adding an alkyl halide, e.g. methyl, propyl iodide etc., to the resulting solution of step (5) to form a crystalline precipitate, adding anhydrous ethanol to the reaction mixture including the precipitate and then filtering the resultant mixture recovering a solid therefrom; and (7) drying the solid of step (6) under reduced pressure to yield 1-alkyl, 4-aza, 1-azonia-bicyclo (2,2,2) octane, 4-oxide, halide.

The foregoing steps involved in the synthesis give good yields, utilize inexpensive reagents and any unreacted starting material, e.g. step (3), can be recycled. Thus, the process is highly efficient and highly affordable.

The invention will be further described in conjunction with the following non-limitative examples.

EXAMPLE 1

Preparation of 1-methyl, 4-aza, 1-azonia-bicyclo (2,2,2) octane, 4-oxide, iodide (a) To 1 mole of 1,4-diazabicyclo(2,2,2)octane (1) (DABCO) dissolved in 1 mole toluene, was added 0.5 moles of 30% aqueous hydrogen peroxide, dropwise and with stirring. Two layers, one aqueous and the other organic were formed.

(b) The aqueous layer was separated from the organic layer, mixed with an equal volume of water and evaporated to dryness under reduced pressure to give a solid, compound (2).

(c) To the solid obtained in step (b) was added 2 moles of toluene to remove unreacted compound (1), the toluene solution was added to the toluene layer obtained in step (a), and the mixture dried over a drying agent such as silica, silica-alumina, or molecular sieves. To the dried toluene solution was then added 1½ fresh moles of compound (1) and the process repeated.

(d) Compound (2) was then placed in a vacuum oven, heated to 120° C. gently while the pressure in the oven was reduced to about 0.5 mm of mercury, and maintained at 120° C. and at a pressure of 0.5 mm mercury for 16 hours, to give compound (3), about 0.8 moles.

(e) Compound (3), 0.8 moles, was then dissolved in 1 mole of anhydrous ethanol to give solution (1).

(f) 0.8 moles of methyl iodide were than added to solution (1) to give a crystalline precipitate. One mole of anhydrous ethanol was then mixed with the reaction mixture of step (f) and the mixture filtered.

(g) The solid recovered from step (f) was then placed in a vacuum oven and dried at 80° C. at a pressure of 0.5 mm, to give 0.75 moles of 1-methyl, 4-aza, 1-azonia-bicyclo (2,2,2)octane, 4-oxide, iodide. M.pt. decomposes 145° C. $^1$Hnmr (D$_2$O) ppm: 3.42 (3H singlet) 4.1 (12H singlet) Found C, 31.0; H, 5.6; N, 10.2; I, 47.1; O, 6.1 Calculated for C$_7$H$_{15}$N$_2$IO: C 31.1; H 5.6; N, 10.4; I, 47.0, O; 5.9

Calculated vs found results were in excellent agreement indicating the compound desired had been obtained.

EXAMPLE 2

Preparation of 1-propyl, 4-aza, 1-azonia-cicyclo (2,2,2)octane, 4-oxide, iodide (a) To 1 mole of 1,4-diazabicyclo(2,2,2)octane (1) (DABCO) dissolved in 1 mole toluene, was added 0.5 moles of 30% aqueous hydrogen peroxide, dropwise and with stirring. Two layers, one aqueous and the other organic were formed.

(b) The aqueous layer was separated from the organic layer, mixed with an equal volume of water and evaporated to dryness under reduced pressure to give a solid, compound (2).

(c) To the solid obtained in step (b) was added 2 moles of toluene to remove unreacted compound (1), the toluene solution was added to the toluene layer obtained in step (a), and the mixture dried over a drying agent such as silica, silica-alumina, or molecular sieves. To the dried toluene solution was then added 1½ fresh moles of compound (1) and the process repeated.

(d) compound (2) was then placed in a vacuum oven, heated to 120° C. gently while the pressure in the oven was reduced to about 0.5 mm of mercury, and maintained at 120° C. and at a pressure of 0.5 mm mercury for 16 hours, to give compound (3), about 0.8 moles.

(e) Compound (3), 0.8 moles, was then dissolved in 1 mole of anhydrous ethanol to give solution (1).

(f) 0.8 moles of propyl iodide were then added to solution (1) to give a crystalline precipitate. One mole of anhydrous ethanol was then mixed with the reaction mixture of step (f) and the mixture filtered.

(g) The solid recovered from step (f) was then placed in a vacuum oven and dried at 80° C. at a pressure of 0.5 mm, to give 0.75 moles of 1-propyl, 4-aza, 1-azonia-bicyclo (2,2,2)octane, 4-oxide, iodide.

What is claimed:

1. As a composition of matter 1-methyl or propyl, 4-aza, 1-azonia-bicyclo(2,2,2)octane, 4-oxide, halides.